United States Patent [19]

Stowe

[11] Patent Number: 4,643,354

[45] Date of Patent: Feb. 17, 1987

[54] MULTI-LAYER POULTRY VACCINATOR

[75] Inventor: John H. Stowe, Westfield, Ind.

[73] Assignee: Curtis-Dyna Products Corporation, Westfield, Ind.

[21] Appl. No.: 693,788

[22] Filed: Jan. 23, 1985

[51] Int. Cl.[4] ...................... B05B 17/04; A61M 11/02

[52] U.S. Cl. ........................................ 239/1; 239/77; 239/167; 239/172; 239/311; 239/373; 239/562; 239/565; 128/200.14

[58] Field of Search .................. 239/76, 77, 164, 170, 239/167, 172, 308, 311, 373, 398, 444, 536, 562, 565, 1, 10, 159, 176; 128/200.14; 604/24

[56] References Cited

U.S. PATENT DOCUMENTS

| | | | |
|---|---|---|---|
| 349,087 | 9/1886 | Dennis | 239/164 X |
| 3,137,446 | 6/1964 | Masuda | 239/76 X |
| 3,163,149 | 12/1964 | Ivey | 239/159 X |
| 3,490,695 | 1/1970 | Rittenhouse | 239/77 |
| 3,521,817 | 7/1970 | Curtis et al. . | |
| 3,777,752 | 12/1973 | Goodwin | 128/200.14 |

FOREIGN PATENT DOCUMENTS

| | | | |
|---|---|---|---|
| 2706526 | 8/1978 | Fed. Rep. of Germany | 239/373 |
| 1163900 | 9/1969 | United Kingdom | 239/77 |

*Primary Examiner*—Joseph F. Peters, Jr.
*Assistant Examiner*—Mary Beth O. Jones
*Attorney, Agent, or Firm*—Woodard, Weikart, Emhardt & Naughton

[57] ABSTRACT

A poultry vaccinator for use in brooding houses having multiple layered rows of cages for high volume vaccination. The vaccinator apparatus includes a plurality of atomizer nozzles disposed at multiple elevations on a collapsible stand pipe assembly. A single reservoir provides a common source for vaccination liquid for each of the atomizer nozzles. Calibration orifices located in the liquid lines to each of the atomizer nozzles provide pressure compensation for elevational differences of the nozzles. Thereby producing a uniform particle size aerosol out of the nozzles regardless of nozzle elevation.

1 Claim, 2 Drawing Figures

MULTI-LAYER POULTRY VACCINATOR

BACKGROUND OF THE INVENTION

The present invention relates generally to the field of poultry vaccinators and, more particularly to such devices wherein the vaccination is accomplished by spraying the poultry.

This invention relates to a machine for treatment of animals in cages which are located adjacent to narrow aisles and which are stacked vertically in multiple layers. It is common knowledge in the poultry industry that poultry can be innoculated for specific diseases, such as New Castle bronchitis by generating mists with particles of controlled size and projecting these particles into close proximity of the poultry such that the particles are ingested through the eyes or nasally. This has been done in the past with machines that require the operator to manually direct the spray mist resulting in uneven distribution and time consuming application. The total time for performing the procedure is critical because the brooding houses must be closed to produce satisfactory results. In warmer weather, closing the houses for more than a few minutes at a time results in intolerable heat build up.

SUMMARY OF THE INVENTION

A multiple layer poultry vaccinator in accordance with the present invention comprises a plurality of atomizing nozzles disposed at multiple elevations, each of the nozzles having an air intake chamber and a liquid intake chamber. There is further provided a reservoir for containing, under elevated pressure, a common source of liquid vaccination serum in flow communication with each of said nozzles. A means is also provided for supplying pressurized liquid from said reservoir to the liquid intake chamber of each of the nozzles and for supplying pressurized air to the air intake chamber of each of the nozzles. The invention further includes a means for regulating an atomized spray out of each of said nozzles so that the particles in said atomized spray have a substantially uniform particle size despite the elevational differences between said nozzles.

It is an object of the present invention to provide an improved poultry vaccinator.

It is also an object of the present invention to provide an improved poultry vaccinator which is capable of vaccinating large quantities of chickens rapidly, thus minimizing the length of time the brooding house must be kept closed without air ventilation.

It is also an object of the present invention to provide an improved poultry vaccinator having atomizing nozzles at different elevations and using a common liquid reservoir to produce uniform distribution of the atomized particles into the poultry cages.

A yet further object of the present invention is to provide an improved poultry vaccinator wherein the particle size of the atomized spray is uniform irrespective of the elevation of the atomizing nozzles.

An additional object is to provide uniform direction of application and distribution of the atomized particles into the poultry cages.

A further object of the present invention is to provide a device with the advantages previously described which is easily adjustable for variations in cage elevation, numbers of rows of cages, etc., and which is collapsible for easy storage and transportation.

It is also an object of the present invention to provide a device with the advantages previously described which is of relatively simple construction and economical to use.

Related objects and advantages of the subject invention will become more apparent by reference to the following figures and detailed description.

DESCRIPTION OF THE PREFERRED EMBODIMENT

Figure 1:
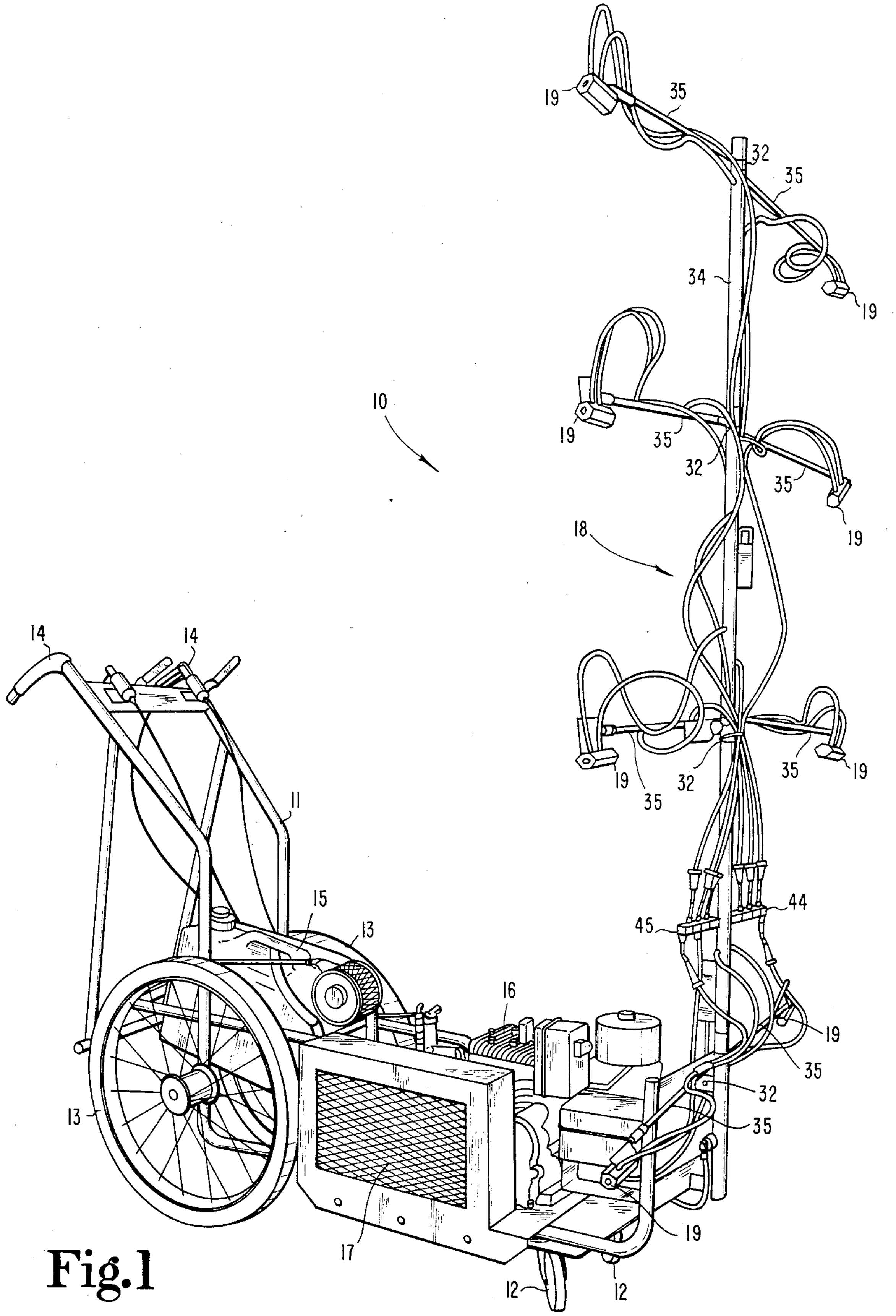
FIG. 1 is a perspective view of the multi-layer poultry vaccinator of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to the drawings in detail, FIG. 1 shows the apparatus of the present invention generally designated at 10. The apparatus 10 generally includes a frame or carriage 11 mounted on front and rear wheels 12 and 13, respectively, and manually pushed by an operator holding handlebars 14. Mounted rearwardly on frame 11 is a tank 15 forming a reservoir for containing the vaccination fluid under pressure. A gasoline internal combustion engine 16 serves as the primary drive means for driving a rotary blower or compressor 17 which provides a continuous supply of air under pressure for atomizing the vaccination liquid and for placing the liquid under pressure. A collapsible air stand pipe assembly 18, mounted forwardly on the carriage 11, distributes air and vaccination fluid to a number of nozzles 19 located at multiple elevations on pipe assembly 18 for dispersing an atomized liquid of substantially uniform particle size. Stand pipe assembly 18 comprises three segments which separate and pivotally collapse for easy shipping and storage.

Figure 2:
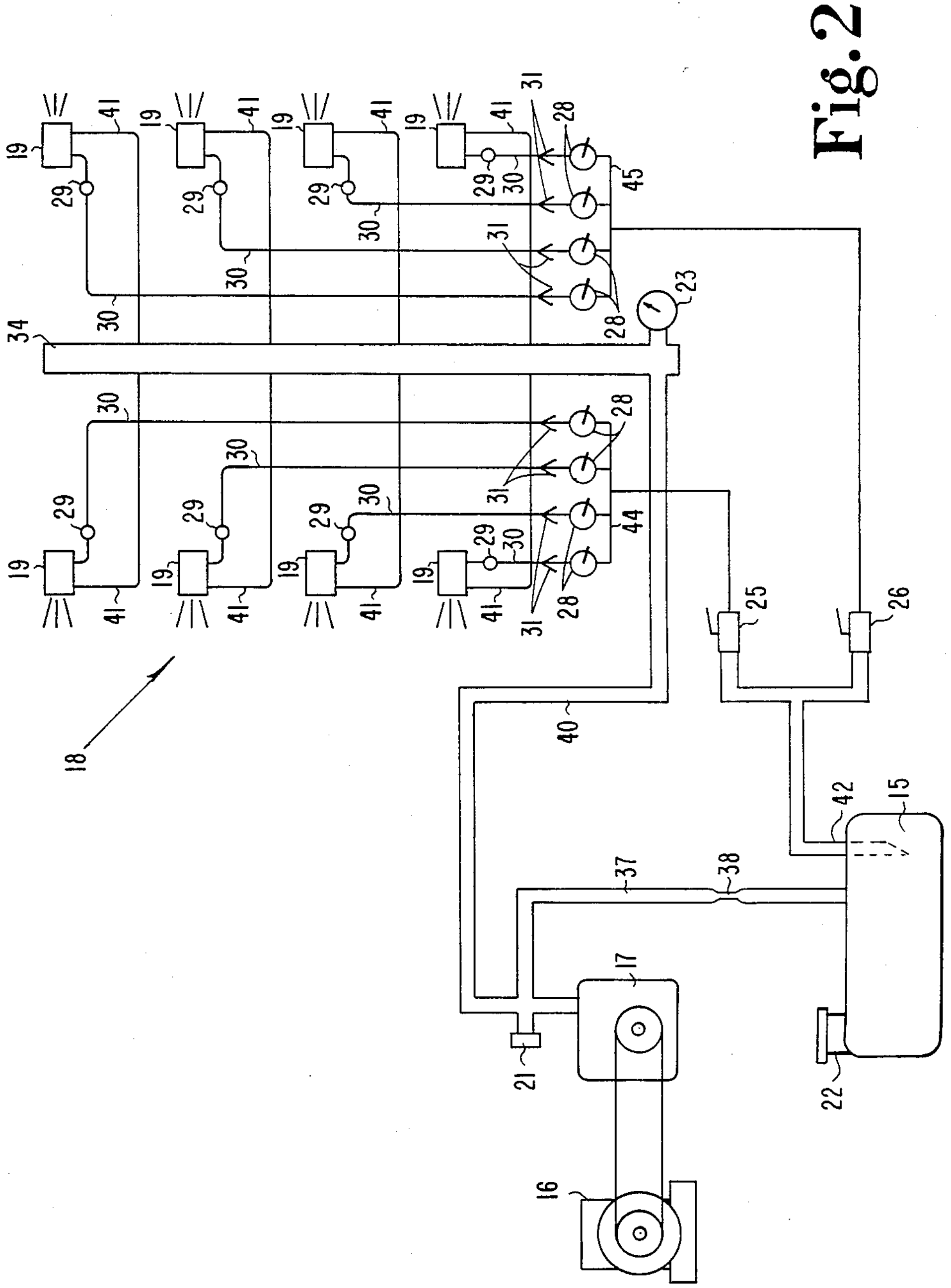
FIG. 2 is a schematic representation of the elements forming the present invention and showing the interconnection of elements.

Referring now also to FIG. 2, a relief valve 21 allows for adjustment of the blower pressure, thus allowing the variation of nozzle pressure for controlling the particle size of the aerosol in different applications. Particle size of the serum will vary according to the age of poultry within the brooding house. A tank bleed valve 22 maintains a relatively constant elevated pressure in the liquid tank 15. A pressure gage 23 allows the monitoring of air pressure in the air distribution system. A multiplicity of output nozzles 19 are of conventional design and may be constructed in accordance with the nozzle shown in U.S. Pat. No. 3,521,817 to Curtis et al. Left and right main shut off valves 25 and 26 respectively control the liquid output of the left and right columns of nozzles 19, or allow simultaneous output. Individual shutoffs 28 are provided for each of the nozzles 19 so that the apparatus 10 can be set up for different quantities of vertically stacked rows of cages. A calibration orifice 29 is provided in the liquid line 30 for each nozzle to compensate for pressure differences due to the head height of liquid at the various nozzle elevations. The liquid line to each nozzle 19 is also provided with a check valve 31 to prevent reverse flow of liquid from higher tubing out the lower nozzles 19 when the blower pressure is turned off.

In the preferred embodiment shown in FIG. 1, there are eight nozzles 19 disposed in pairs vertically spaced apart along stand pipe assembly 18. Thus, the pairs of nozzles produce an atomized spray of the vaccination serum at four predetermined elevations. The elevation of each pair of nozzles 19 may be adjusted vertically up or down to correspond to the elevations of the poultry cages by adjusting the position of the respective clamp 32 on air stand pipe 34. A pair of arms 35 extend outwardly left and right from each clamp 32. Each of the arms 35 pivots in the plane of the stand pipe 34 to allow the arms to collapse for storage purposes or to adjust the height of the respective nozzles without having to adjust the height of the clamp on stand pipe 34. Each of the arms 35 is comprised of two telescoping sections which permit the position of the nozzle to be adjustable laterally outwardly from the stand pipe 34. Each nozzle is pivotally mounted at the end of its respective arm and pivots in the plane of the stand pipe 34. Thus, the nozzles can be adjusted on their respective arms so as to be directed in a horizontal direction even when the corresponding arm is oriented in a direction other than horizontally.

The operation of the apparatus 10 may be described as follows. Engine 16 is manually started, driving the rotary blower or compressor 17 and generating air under pressure at 5 to 15 psi. The pressurized air is routed via separate routes, one through line 37 having a limiting orifice 38 and into the sealed tank 15 where it pressurizes the liquid to a pressure determined by the tank air pressure bleed valve 22. The other route is through line 40 and directly to the air stand pipe 34, the air being tapped at multiple levels on pipe 34 by individual air lines 41 leading to each of the atomizing nozzles 19. The pressure relief valve 21 allows the pressure in line 40 to be adjusted to a desired predetermined level. As the pressure in line 40 builds to the desired level, the pressure of the liquid inside tank 15 builds to a predetermined level controlled by the orifice 38 and bleed valve 22. The pressurized liquid is forced through the tank stand pipe 42 to the left and right shut off valves 25 and 26, respectively, which may be independently opened or closed to control the flow of fluid to the corresponding left and right manifolds 44 and 45. The flow of liquid into each of the nozzle lines 30 is individually controlled by individual shut off valves 28 to allow for operation of any combination of the nozzles, as desired. With respect to each of the nozzles, the liquid flows into the nozzle where it is atomized into an aerosol by pressurized air flowing through the nozzle from air line 41. The individual check valves 31 prevent draining of liquid from the tubing and nozzles at higher elevations through lower nozzles. The aerosol particles are projected in a spray of substantially uniform size, density and area coverage into a poultry population housed in rows of vertically stacked cages.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of innoculating chickens housed in multiple rows of vertically stacked cages, comprising the steps of:

(a) providing a hand-propelled wheeled poultry vaccinator adapted for vaccination of poultry in multilayer cages, said poultry vaccinator having a plurality of atomizing spray nozzles disposed at multiple elevations, each of said nozzles having an air intake chamber and a liquid intake chamber, a reservoir for containing, under elevated pressure, a common source of liquid vaccination serum in flow communication with each of said nozzles, a means for supplying pressurized liquid from said reservoir to the liquid intake chamber of each of said nozzles and for supplying pressurized air to the air intake chamber of each of said nozzles, and a means for regulating an atomized spray out of each of said nozzles so that the particles in said atomized spray have a substantially uniform particle size despite the elevational differences between said nozzles;

(b) adjusting the height of said atomizing spray nozzles to correspond to the height of each of the rows of vertically stacked cages; and (c) pushing the poultry vaccinator along said rows of vertically stacked cages while spraying the poultry in the cages with a uniform particle size atomizing spray of the liquid vaccination serum generated from said atomizing spray nozzles at elevations corresponding to the height of the vertically stacked cages.

* * * * *